United States Patent [19]

Ariga et al.

[11] 4,198,340
[45] Apr. 15, 1980

[54] PROCESS FOR STEREOISOMERIZATION OF CIS-3-METHYL-Δ[4]-TETRAHYDRO-CIS,CIS-PHTHALIC ANHYDRIDE

[75] Inventors: Nagao Ariga, Chiba; Minoru Yamamoto, Ichihara; Katsuji Takahashi, Chiba; Takehisa Mizuno, Ichihara, all of Japan

[73] Assignee: Dainippon Ink & Chemicals, Inc., Tokyo, Japan

[21] Appl. No.: 22,112

[22] Filed: Mar. 20, 1979

[51] Int. Cl.[2] .......................................... C07D 307/89
[52] U.S. Cl. ................................................. 260/346.3
[58] Field of Search ........................... 260/346.7, 346.3

[56] References Cited
PUBLICATIONS
Craig, JACS, vol. 72, (1950), pp. 1678–1681.

Primary Examiner—Richard Raymond
Attorney, Agent, or Firm—Sherman & Shalloway

[57] ABSTRACT

A process is provided for isomerizing (1) cis-3-methyl-Δ[4]-tetrahydro-cis,cis-phthalic anhydride into (2) trans-3-methyl-Δ[4]-tetrahydro-cis,cis-phthalic anhydride, which is its stereoisomer, by heating the compound (1) preferably at a temperature of 100° to 250° C. in the presence of an alkali metal compound such as lithium hydroxide, sodium hydroxide or sodium acetate. A mixture of said compounds (1) and (2) in a ratio by weight of 7:3 to 2:8 obtained by the isomerization reaction is liquid at room temperature and can be used advantageously as a curing agent for epoxy resins.

2 Claims, 1 Drawing Figure

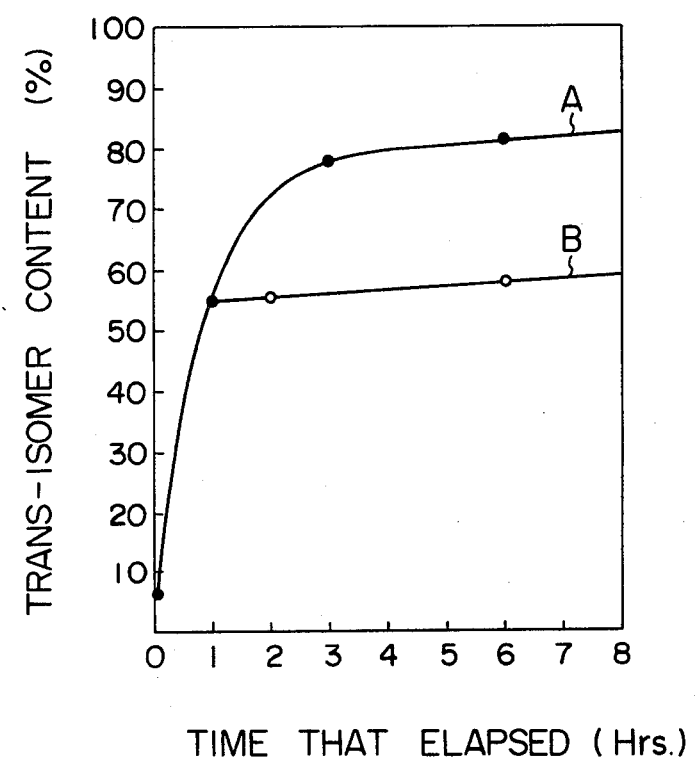

PROCESS FOR STEREOISOMERIZATION OF CIS-3-METHYL-$\Delta^4$-TETRAHYDRO-CIS,CIS-PHTHALIC ANHYDRIDE This invention relates to a process for isomerizing cis-3-methyl-$\Delta^4$-tetrahydro-cis,cis-phthalic anhydride (may be referred to hereinafter simply as "cis-tetrahydro") into its stereoisomer, trans-3-methyl-$\Delta^4$-tetrahydro-cis,cis-phthalic anhydride (may be hereinbelow referred to simply as "trans-tetrahydro"). The invention also concerns a process for isomerizing a hydrogenated product of the cis-tetrahydro, cis-3-methyl-hexahydro-phthalic anhydride (may be referred to hereinafter simply as "cis-hexahydro"), into its stereoisomer, trans-3-methyl-hexahydro-phthalic anhydride (may be referred to hereinafter simply as "trans-hexahydro").

The cis-tetrahydro (otherwise called cis-3-methyl-4-cyclohexene-cis,cis-1,2-dicarboxylic acid anhydride) formed by the Diels-Alder reaction between trans-piperylene and maleic anhydride is known to be useful as a component of air-drying polyesters, but because it has a melting point of 63° to 65° C., it is inconvenient to handle. The trans-tetrahydro which is a stereoisomer of the cis-tetrahydro with regard to the methyl group, on the other hand, has a melting point as low as 31° C., and when mixed with the cis-tetrahydro, forms a eutectic mixture having an even lower melting point and being liquid at room temperature. Such a dicarboxylic acid anhydride being liquid at room temperature is easy to handle and convenient for use as a curing agent for epoxy resins. The reaction in which the trans-tetrahydro is formed by the stereoisomerization of the cis-tetrahydro, therefore, is of high importance from the commercial point of view.

The cis-hexahydro obtained by hydrogenation of the cis-tetrahydro is liquid at room temperature, and hence, is used as a curing agent for epoxy resins for use in casting, potting or encapsulation, or in impregnation, or in solventless varnishes. The trans-hexahydro obtained by stereoisomerization of the cis-hexahydro is a solid having a melting point of 70° C. and can be used as a curing agent for epoxy powder paints. Therefore, the reaction where the trans-hexahydro is formed by stereoisomerization of the cis-hexahydro is also important commercially.

In regard to the above-mentioned types of stereoisomerization reaction, David Craig, J. Am. Chem. Soc., Vol. 72, pp. 1678–1681 (1950) discloses a process involving the use of dibutylaniline as an isomerization catalyst. This process, however, has such defects that a considerably large amount of the catalyst is required to obtain an isomerization rate necessary and enough to achieve production on a commercial scale, and that the isomerization of the cis-tetrahydro tends to form a polymer owing to a side-reaction.

The object of the present invention is to provide a process for the stereoisomerization of the cis-tetrahydro or cis-hexahydro, said process obviating said drawbacks of the conventional process and being more suitable for commercial-scale production.

We have found that the use of an alkali metal compound as an isomerization catalyst, even when in a very tiny amount such as 100 ppm or less, permits an isomerization reaction to proceed quickly and enables the amount of a polymer formed as by-product to decrease.

Thus, the present invention provides a process which comprises isomerizing the cis-tetrahydro or cis-hexahydro by heating in the presence of an alkali metal compound to form the trans-tetrahydro or trans-hexahydro that is a stereoisomer of each.

The alkali metal compound usable in the present invention includes, for example, hydroxides of alkali metals, such as lithium hydroxide, sodium hydroxide and potassium hydroxide; oxides of alkali metals, such as lithium oxide, sodium oxide and potassium oxide; alkali metal salts, such as mono- or di-lithium, sodium or potassium salts of aluminic acid, carbonic acid, phosphoric acid, acetic acid, oxalic acid, benzoic acid and 3- or 4-methyl-tetrahydrophthalic acid; lithium chloride; and alcoholates or phenolates of alkali metals expressed by the general formula ROMe in which R represents an alkyl group with 2 to 18 carbon atoms or an aryl group, and Me represents a lithium, sodium or potassium atom.

The amount of the alkali metal compound used is not particularly restricted, but preferably, is in the range of 10 to 5,000 ppm based on the cis-tetrahydro or cis-hexahydro. When the catalyst is used in such an amount, it becomes possible to omit a procedure of removing the catalyst from the reaction product.

The temperature applicable to the stereoisomerization reaction can be varied suitably according to the type or amount of the catalyst used, but generally, it is preferred that the temperature be in the range of 100° to 250° C., more preferably in the range of 150° to 200° C. If this temperature is too low, the rate of reaction becomes slow, while if the temperature is too high, considerable coloration occurs in the resulting product or the aforementioned side-reaction proceeds markedly.

The stereoisomerization reaction is performed, for instance, by heating the cis-tetrahydro or cis-hexahydro at the aforesaid temperature under atmospheric pressure or elevated pressure with the addition of the catalyst. If desired, such an inert solvent as toluene, xylene or tetralin can be used as a reaction medium. In this case, the reaction may be performed using a reaction system mixed with another carboxylic acid anhydride causing no isomerization, such as 4-methyl-$\Delta^4$-tetrahydrophthalic anhydride.

To obtain a reaction product being liquid at room temperature by such stereoisomerization reaction, it is necessary that the reaction be stopped at a time when a mixture of the cis-tetrahydro and its stereoisomer, the trans-tetrahydro, in a weight ratio of 7:3 to 2:8 has been formed in the reaction system. For this purpose, it is a general practice to deactivate the catalyst by lowering the temperature of the reaction system to, say, room temperature to 50° C. Alternatively, the reaction can be stopped immediately by adding phosphorous acid esters such as triphenyl phosphite. This technique of stopping the reaction by the addition of phosphorous acid esters has the following advantages: First, it exhibits an immediate and assured effect as compared with said temperature-lowering technique. Secondly, it is more useful because of its freedom from the drawback that isomerization reaction further proceeds upon heat involved in distilling the resulting mixture for purification.

Examples of said phosphorous acid esters include compounds of the general formula

(RO)$_3$P wherein R represents an alkyl group with 4 to 18 carbon atoms or an aryl group,
such as triphenyl phosphite, tricresyl phosphite, tributyl phosphite or tridecyl phosphite. The amount of the phosphorous acid ester used is at least 1 mole, preferably 1 to 10 moles, per mole of the aforementioned alkali metal compound.

The present invention will be described in more detail with reference to Referential Examples, Comparative Example, Examples and attached drawing. In the Referential Examples, Comparative Example and Examples, parts and percents are all by weight. The attached drawing is a graph illustrating the effect of a reaction terminator in connection with Example 3.

REFERENTIAL EXAMPLE 1

(Preparation of cis-3-methyl-$\Delta^4$-tetrahydro-cis,cis-phthalic anhydride)

A four-necked flask having a volume of 1 liter and equipped with a thermometer, a dropping funnel, a nitrogen introducing tube, and a cooling device was charged with 196 g (2 mols) of maleic anhydride, and 100 g of toluene was further added, followed by heating the mixture to 40° C. While introducing nitrogen through the nitrogen introducing tube, 567 g of a commercially available $C_5$ fraction containing 40% of trans-piperylene and having the composition shown in the table below was added dropwise through the dropping funnel to carry out the Diels-Alder reaction. Since the reaction generated heat, the reaction temperature was maintained at 40° to 50° C. by cooling.

| Composition of $C_5$ fraction | |
|---|---|
| Trans-piperylene | 40% |
| Cis-piperylene | 24% |
| Cyclopentane | 12% |
| Cyclopentene | 17% |
| 3-Methylpentane | 5% |
| 2-Methylpentane | 1% |
| Isoprene | 0.5% |
| Cyclopentadiene | 0.5% |

The total amount of the $C_5$ fraction was added over the course of 30 minutes to 2 hours, and when the reaction was complete, the unreacted $C_5$ fraction and toluene were removed by distillation, thereby to obtain 332 g of a white solid having a melting point of 58° to 61° C.

Analysis by gas chromatography showed that the white solid consisted of 93% of cis-3-methyl-$\Delta^4$-tetrahydro-cis,cis-phthalic anhydride (i.e. cis-tetrahydro) and 7% of its trans-isomer (i.e. trans-tetrahydro).

EXAMPLE 1

1,000 parts of the mixture of 93% cis-tetrahydro and 7% trans-tetrahydro obtained in Referential Example 1 was heated to 175° C., and then, 100 ppm, based thereon, i.e. 0.1 part, of lithium hydroxide was added. The mixture was maintained for 5 hours at 175° C. for the isomerization reaction. Then, the temperature of the reaction mixture was lowered to 30° C. for termination of the reaction.

Distillation of the reaction product afforded 947 parts of a colorless liquid having a boiling point of 130°–135° C./5 mmHg and a solidifying point of 4° C. (Yield: 94.7%)

Gas chromatography analysis showed that the colorless liquid consisted of 38% cis-tetrahydro and 62% trans-tetrahydro.

Additionally, 53 parts of an undistillable polymer remained as a still-bottom product.

COMPARATIVE EXAMPLE

The procedure of Example 1 was repeated except that dibutylaniline was used as a catalyst in an amount of 10 parts per 1,000 parts of the mixture consisting of 93% cis-tetrahydro and 7% trans-tetrahydro obtained in Referential Example 1 and that the isomerization reaction time was elongated to 11 hours. As a result, there was obtained 850 parts of a mixture consisting of 40% cis-tetrahydro and 60% trans-tetrahydro (boiling point 130°–135° C./5 mmHg; solidifying point 3° C.) in a yield of 85%.

150 Parts of an undistillable polymer remained as a still residue.

EXAMPLE 2

1,000 Parts of the mixture of 93% cis-tetrahydro and 7% trans-tetrahydro obtained in Referential Example 1 was heated to 200° C., and 5 parts of sodium hydroxide was added. The mixture was maintained for 1 hour at the same temperature for isomerization reaction, and then cooled to 30° C. for termination of the reaction.

Distillation of the reaction product gave 900 parts of a mixture of 22% cis-tetrahydro and 78% trans-tetrahydro (boiling point 131°–134° C./5 mmHg; solidifying point 27° C.) in a yield of 90%, and 100 parts of an undistillable polymer remained as a still-bottom product.

EXAMPLE 3

1,000 Parts of the mixture of 93% cis-tetrahydro and 7% trans-tetrahydro obtained in Referential Example 1 was heated to 200° C., and 0.1 part of lithium hydroxide was added. The mixture was maintained at the same temperature for 8 hours. During this period, sampling was conducted at time intervals so that trans-isomer content of the reaction mixture was traced by gas chromatography analysis.

Separately, the starting material and the catalyst were charged into another reactor, and maintained for 1 hour at 200° C. When this period passed, 2 parts of triphenyl phosphite was added. Then, the mixture was kept at the same temperature for 7 hours. During this period, the reaction mixture was sampled at time intervals to trace the trans-isomer content of the reaction mixture by gas chromatography analysis.

The attached drawing shows the relationship between the time that elapsed and the trans-isomer content traced in case the reaction terminator was not added (curve A) and in case it was added (curve B). This graph clearly demonstrates that the addition of triphenyl phosphite as a reaction terminator brings forth an immediate termination of the isomerization reaction.

EXAMPLE 4

1,000 Parts of the mixture of 93% cis-tetrahydro and 7% trans-tetrahydro obtained in Referential Example 1 was heated to 175° C., and then 0.2 parts (200 ppm) of sodium acetate was added, followed by maintaining the mixture at the same temperature for 2 hours. Then, 2 parts (2,000 ppm) of tridecyl phosphite was added to terminate the reaction.

The resulting reaction product was distilled to afford 957 parts of a colorless liquid having a boiling point of 175°–180° C./30 mmHg and a solidifying point of 3° C. in a yield of 95.7%, with 43 parts of an undistillable polymer remaining as a bottom residue.

Gas chromatography analysis showed that the colorless liquid was a mixture consisting of 41% cis-tetrahydro and 59% trans-tetrahydro.

REFERENTIAL EXAMPLE 2

(Preparation of cis-3-methyl-hexahydrophthalic anhydride)

To 100 parts of the mixture of 93% cis-tetrahydro and 7% trans-tetrahydro obtained in Referential Example 1 was added 5 parts of a Raney nickel catalyst, and the hydrogenation was carried out at a temperature of 110° C. and a pressure of 50 kg/cm². Then, the catalyst was removed by filtration, and the filtrate was distilled to afford 95 parts of a colorless transparent liquid having a boiling point of 140°–145° C./10 mmHg. This liquid was found by gas chromatography analysis to be a mixture consisting of 90% cis-hexahydro and 10% trans-hexahydro.

EXAMPLE 5

1,000 Parts of the mixture of 90% cis-hexahydro and 10% trans-hexahydro obtained in Referential Example 2 was heated to 200° C., and 0.5 part of sodium hydroxide was added. The mixture was maintained at the same temperature for 1 hour to afford a white crystalline solid partially including an oily substance. The oily substance was removed from the crystalline solid by filtration to yield 750 parts of trans-hexahydro having a melting point of 68°–70° C.

What is claimed is:

1. A process for isomerizing cis-3-methyl-$\Delta^4$-tetrahydro-cis,cis-phthalic anhydride into its stereoisomer, trans-3-methyl-$\Delta^4$-tetrahydro-cis,cis-phthalic anhydride, which comprises heating cis-3-methyl-$\Delta^4$-tetrahydro-cis,cis-phthalic anhydride in the presence of an alkali metal compound.

2. A process for isomerizing cis-3-methyl-$\Delta^4$-tetrahydro-cis,cis-phthalic anhydride, which comprises heating cis-3-methyl-$\Delta^4$-tetrahydro-cis,cis-phthalic anhydride in the presence of an alkali metal compound to obtain a mixture of cis-3-methyl-$\Delta^4$-tetrahydro-cis,cis-phthalic anhydride and its stereoisomer, trans-3-methyl-$\Delta^4$-tetrahydro-cis,cis-phthalic anhydride, in a ratio by weight of 7:3 to 2:8.

* * * * *